United States Patent [19]

Dekker et al.

[11] Patent Number: 5,698,253
[45] Date of Patent: Dec. 16, 1997

[54] DIMETHYL-CYCLOHEXANECARBOXYLIC ACID ESTERS IN PERFUMERY

[76] Inventors: Enno E. J. Dekker, Dirk Tersteeglaan 44, 1411 MB Naarden; Johan L. de Bruine, Spengen 2, 3628 EX, Kockengen, both of Netherlands

[21] Appl. No.: 454,219
[22] PCT Filed: Dec. 9, 1993
[86] PCT No.: PCT/EP93/03548
§ 371 Date: Apr. 29, 1996
§ 102(e) Date: Apr. 29, 1996
[87] PCT Pub. No.: WO94/13766
PCT Pub. Date: Jun. 23, 1994

[30] Foreign Application Priority Data

Dec. 13, 1992 [NL] Netherlands ............ 92203880.7

[51] Int. Cl.[6] ................................................ A23L 1/22
[52] U.S. Cl. ................ 426/538; 131/276; 252/522; 560/1
[58] Field of Search ............... 252/522; 560/1; 426/538; 131/276

[56] References Cited

U.S. PATENT DOCUMENTS 3,910,963  10/1975  Souma et al. ............... 260/343
4,439,353  3/1984   Schenk ........................ 252/522

Primary Examiner—Terressa Mosley
Attorney, Agent, or Firm—Cushman Darby & Cushman IP Group Pillsbury Madison & Sutro LLP

[57] ABSTRACT

The invention concerns perfumes containing as fragrance materials 1,4-dimethyl-cyclohexane-1-carboxylic acid esters of general formula wherein R is an alk(en)yl group having 1–4 carbon atoms, preferably R$(1,3)methyl. The fragrance materials have very agreable fresh herbal ordours with green and floral notes.

8 Claims, No Drawings

DIMETHYL-CYCLOHEXANECARBOXYLIC ACID ESTERS IN PERFUMERY

This is a 371 of PCT/EP93/03548 filed Dec. 9, 1993.

The present invention relates to the use of certain dimethyl-cyclohexanecarboxylic acid esters as fragrance materials and to perfumes and perfumed products containing these compounds.

Many synthetic perfume components have been developed, especially in the last decades to substitute known perfume materials of natural origin. Nevertheless there is a constant need for new synthetic perfume components which are more stable than those previously developed and/or have additional or more delicate odour notes to further complete the fragrance palette from which the perfumer can chose in composing perfumes which are suitable also for various agressive environments.

Various substituted cyclohexene- and cyclohexadienecarboxylic acid esters are known as fragrance materials in the art of perfumery. The majority of them are of the 2,6,6-trimethyl- or the 2-ethyl-6,6-dimethyl-substituted type and were developed in analogy to various compounds found in nature possessing the 2,6,6-trimethylcyclohexene moiety. Such compounds, with the double bond in the 1- or 2-position and sometimes containing an additional methyl group in the 3-position are described e.g. in EP-A-0 056 109, GB 1 497 498 and U.S. Pat. No. 4,375,001 and various other patents and patent applications mentioned therein. In EP-A-0 053 704 corresponding 2,3,6,6-tetramethyl- and 2-ethyl-6,6-dimethyl-cyclohexane-1-carboxylic acid esters are described. Thus, these compounds are all heavily substituted with methyl and ethyl groups. The odors reported may vary considerably although in many cases fruity and floral, especially roselike dours are reported.

In EP-A-0 199 330 1,4,6-trimethylcyclohex-3-ene derivatives, including methyl 1,4,6-trimethylcyclohex-3-ene-1-carboxylate, are reported to be of use in perfumery. They appear to have mostly herbal woody, even patchouli-like, odors and thus appear to be distincty different in odour character from the 2,6,6- and 2,3,6,6-substituted cyclohexenecarboxylic acid esters reported above. In EP-A-0 199 330 this is attributed to the presence of the quaternary carbon atom in the 1-position. Nevertheless, methyl 1-methylcyclohex-3-ene-1-carboxylate, which is marketed as a fragrance material, has a predominantly fruity odour, which seems to be in contradiction with this rule.

Ethyl 2,4-dimethyl-cyclohexane-1- carboxylate, on the other hand, is also marketed as a fragrance material, but with a distinctly floral odour.

Methyl and butyl 1,4-dimethylcyclohex-3-ene-1-carboxylate stereoisomers have been descibed in CH-A-680 853. The (−)-S methylester is described to have a rather uninteresting herbal, humus and woody and also slightly chemical type of odour whereas the (+)-R isomer has an agreeable fresh fruity-menthol-anis-like odour. The racemic mixture is describes as being spoiled from a perfumery point of view by the odour contribution of the (−)-S isomer.

Finally, in U.S. Pat. No. 4,392,976 4-methyl-cyclohex-3-ene-1-carboxylic acid is reported to have a cumin-like odour. No mention is made of any esters of this acid.

It has now been found that 1,4-dimethylcyclohexane-1-carboxylic acid esters of the general formula:

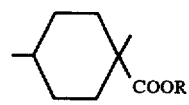

wherein R is an alk(en)yl group having 1–4 carbon atoms, are valuable fragrance materials having very agreeable fresh herbal odours with green and floral notes. The methyl esters are especially preferred. Although the methyl esters are known as such, e.g. from H. van Bekkum et al, Recl. Tray. Chim. Pays-Bas, 88(3) 301–6, 1969 and from W. G. Schindel, R. E. Pincock, J. Org. Chem., 35960, 1789–94, 1970, no mention is made of any organoleptic property.

The compounds may be prepared by methods known in the art, particularly by Diels-Alder reaction of the corresponding methacrylate ester with isoprene, followed by hydrogenation and separation of the 1,3-dimethyl from the 1,4-dimethyl esters. A mixture of cis-dimethyl and trans-dimethyl esters is thus obtained which may be separated into its components by methods described in the art, e.g. by W. G. Schindel, vide supra. Also the racemic micture obtained may be separated according to methods known in the art e.g. as decribed in CH-A-680 853 above. However, contrary to what is desribed therein, for the use of the compounds of this invention as fragrance material such separations are superfluous.

The esters according to the invention may be used as such to give various odour notes of the floral, green and fruity type to all sort of products, or they may be incorporated in perfumes. For the purposes of this invention a perfume is defined as a mixture of various fragrance materials, if desired dissolved in a suitable solvent or mixed with a solid substrate, which is used to provide a desired odour to the skin or to all sorts of products. Examples of such perfumed products are: fabric washing powders and liquids and other fabric care products; detergents and household cleaning, scouring and disinfection products; air fresheners, room sprays and pomanders; candles; soaps, shampoos and other personal cleaning products; cosmetics such as creams, ointments, toilet waters, preshave-, aftershave- and other lotions, talcum powders, body deodorants and antiperspirants.

Known fragrance materials which may be advantageously combined with the esters according to the invention may be natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds. Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with the esters according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert-butyl cyclohexyl acetate, isononyl acetate, vetiveryl acetate, vetiverol, α-hexylcinnamaldehyde, 2-methyl-3-(p-tert-butylphenyl)

propanal, 2-methyl-3-(p-isopropylphenyl)propanal, 3-(p-tert-butylphenyl)-propanal, tricyclodecenyl acetate, tricyclodecenyl propionate, 4-(4-hydroxy-4-methyl-pentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks tetralin musks isochroman musks macrocyclic ketones, macrolactone musks ethylene brassylate, aromatic nitromusks.

Solvents which can be used in perfume compositions which contain compounds according to the invention are, for example: ethanol, isopropanol, diethylene glycol monoethyl ether, dipropylene glycol, diethyl phthalate, triethyl citrate, etc.

The quantities in which the esters according to the invention can be used in perfumes or in products to be perfumed may vary within wide limits and depend, inter alia, on the nature of the product, on the nature and the quantity of the other components of the perfume in which the compounds are used and on the olfactive effect desired. It is therefore only possible to specify wide limits, which, however, provide sufficient information for the specialist in the art to be able to use the esters according to the invention for his specific purpose. In perfumes an amount of 0.01% by weight or more of the esters according to the invention will generally have a clearly perceptible olfactive effect. Preferably the amount is 0.1% by weight and may be up to 80% by weight. The amount of esters according to the invention present in products will generally be at least 0.5 ppm by weight.

The following examples are only intended to illustrate the preparation and use of the esters according to the invention, but the invention is not in any way limited thereto

EXAMPLE 1

Synthesis of methyl 1,4-dimethylcyclohexane-1-carboxylates

A mixture of methyl methacrylate (135 g; 1.4 mol) and isoprene (137 g; 2.0 mol) in a pressurized reaction vessel was quickly heated to 250° C., kept at that temperature for 100 minutes and quickly cooled to room temperature. The crude reaction mixture obtained (270 g) comprised 75% of the cyclohexene-carboxylates and only minor amounts of starting materials.

This mixture was hydrogenated at 100° C. and atmospheric pressure using about 200 mg 5% palladium on carbon as a catalyst. The dimethyl-cyclohexane-carboxylates in the crude reaction mixture after hydrogenation consisted of 23% 1,3-dimethyl- and 77% 1,4-dimethyl isomers. This mixture was carefully fractionated under reduced pressure yielding 94 g (35%) of perfumery grade product (Bpt. 85°–87° C. at 2 kPa). This product consisted of 17% 1,3-dimethyl isomers, 51.5% trans-1,4-dimethyl isomer and 31.5% cis-1,4-dimethyl isomer.

EXAMPLE 2

A herbaceous floral perfume for use in household products at 0.2% was prepared according to the following recipe.

| | |
|---|---|
| Iso bornyl acetate | 40.0 |
| Iso-longifolanone (Q) | 11.0 |
| Dihydromyrcenol (Q) | 7.0 |
| Jasmacyclene (Q) | 6.0 |
| Linalyl acetate | 6.0 |
| Acetyl cedrene (Q) | 5.0 |
| Benzyl acetate | 4.0 |
| Geranyl acetate | 4.0 |
| β-Phenoxyethyl isobutyrate (Q) | 4.0 |
| Linalool | 3.5 |
| Camphor powder | 3.0 |
| Patchouli acid washed (Q) | 2.0 |
| Dipropylene glycol | 1.5 |
| Olibanum oil | 1.0 |
| Methyl 1,4-dimethylcyclo-hexane-1-carboxylate | 2.0 |
| Total: | 100 |

(Q) marketed by Quest International, Ashford, Kent, UK.

The addition of Methyl 1,4-dimethylcyclo-hexane-1-carboxylate makes the odour of the perfume much more sophisticated by adding a more rounded herbal character.

We claim:

1. Perfume comprising at least 0.01% by weight of at least one 1, 4-dimethylcyclohexane-1-carboxylic acid ester according to the general formula:

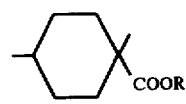

wherein R is an alk(en)yl group having 1–4 carbon atoms.

2. Perfume according to claim 1 wherein R is a methyl group.

3. Perfume according to claims 1 or 2 wherein the amount of 1,4-dimethylcyclohexane-1-carboxylic acid ester is at least 0.1% by weight.

4. Perfume products comprising at least 0.5 ppm by weight of at least one 1,4-dimethylcyclohexane-1-carboxylic acid ester according to the general formula:

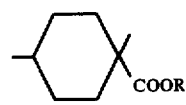

wherein R is an alk(en)yl group having 1–4 carbon atoms.

5. Perfumed products according to claim 4 wherein R is a methyl group.

6. In a process for preparing perfumed products, the improvement for enhancing odor of the product which comprises adding to the product at least 0.5 ppm by weight at least one 1, 4-dimethylcyclohexane-1-carboxylic acid ester according to the general formula:

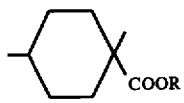

wherein R is an alk(en)yl group having 1–4 carbon atoms to provide the product with a fresh herbal green odor note.

7. Process according to claim 6 wherein R is a methyl group.

8. A process for obtaining a perfumed effect which comprises applying to an area requiring said effect, an effective amount of a compound according to claim 1.

* * * * *